United States Patent
Hu et al.

(10) Patent No.: US 10,353,006 B2
(45) Date of Patent: Jul. 16, 2019

(54) SYSTEM AND METHOD FOR ATTENUATION CORRECTION

(71) Applicant: SHANGHAI UNITED IMAGING HEALTHCARE CO., LTD., Shanghai (CN)

(72) Inventors: Lingzhi Hu, Shanghai (CN); Yang Lyu, Shanghai (CN); Qinghua Li, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

(21) Appl. No.: 15/638,354

(22) Filed: Jun. 29, 2017

(65) Prior Publication Data

US 2018/0231612 A1    Aug. 16, 2018

Related U.S. Application Data

(63) Continuation of application No. PCT/CN2017/073449, filed on Feb. 14, 2017.

(51) Int. Cl.
| | |
|---|---|
| *G01R 31/34* | (2006.01) |
| *G01T 1/16* | (2006.01) |
| *G01T 1/29* | (2006.01) |
| *G01R 33/34* | (2006.01) |
| *G01R 33/48* | (2006.01) |
| *A61B 6/00* | (2006.01) |
| *A61B 6/03* | (2006.01) |

(Continued)

(52) U.S. Cl.
CPC ..... *G01R 31/346* (2013.01); *G01R 33/34084* (2013.01); *G01R 33/481* (2013.01); *G01T 1/1603* (2013.01); *G01T 1/2985* (2013.01); *A61B 6/037* (2013.01); *A61B 6/4417* (2013.01); *G01R 31/343* (2013.01); *G01R 33/34007* (2013.01); *G01R 33/54* (2013.01); *G01R 33/56391* (2013.01); *G01R 33/58* (2013.01)

(58) Field of Classification Search
CPC .... G01R 31/06; G01R 31/346; G01R 31/343; G01R 31/34; G01R 31/027
USPC ........................................... 324/546
See application file for complete search history.

(56) References Cited

U.S. PATENT DOCUMENTS

| | | |
|---|---|---|
| 2011/0123083 A1 | 5/2011 | Ojha et al. |
| 2011/0317900 A1 | 12/2011 | Pal et al. |

(Continued)

FOREIGN PATENT DOCUMENTS

| | | |
|---|---|---|
| CN | 203433927 U | 2/2014 |
| CN | 205193262 U | 4/2016 |
| CN | 205720622 U | 11/2016 |

OTHER PUBLICATIONS

Paulus, Daniel H., L. Tellmann, and Harald H. Quick. "Towards improved hardware component attenuation correction in PET/MR hybrid imaging." Physics in Medicine & Biology 58.22 (2013): 8021. (Year: 2013) (Year: 2013).*

Malone, Ian B., et al. "Attenuation correction methods suitable for brain imaging with a PET/MRI scanner: a comparison of tissue atlas and template attenuation map approaches." Journal of Nuclear Medicine 52.7 (2011): 1142._ (Year: 2011).*

International Search Report in PCT/CN2017/073449 dated Oct. 30, 2017, 7 pages.

Written Opinion in PCT/CN2017/073449 dated Oct. 30, 2017, 5 pages.

(Continued)

*Primary Examiner* — Christopher P McAndrew
(74) *Attorney, Agent, or Firm* — Metis IP LLC

(57) ABSTRACT

The present disclosure relates to systems and methods for attenuation correction. The system includes a coil module, which includes a flexible coil and a supporter. The supporter may be configured to hold the flexible coil. The flexible coil may be deformed to form a receiving space.

21 Claims, 12 Drawing Sheets

(51) Int. Cl.
G01R 33/54 (2006.01)
G01R 33/58 (2006.01)
G01R 33/563 (2006.01)

(56) References Cited

U.S. PATENT DOCUMENTS

| | | | |
|---|---|---|---|
| 2013/0006091 A1 | 1/2013 | Manjeshwar et al. | |
| 2013/0266198 A1* | 10/2013 | Pereira | G06T 7/0012 382/131 |
| 2014/0187910 A1 | 7/2014 | Culver et al. | |
| 2014/0193054 A1* | 7/2014 | Blaffert | G01R 33/481 382/131 |
| 2014/0221817 A1* | 8/2014 | Aklan | G01R 33/481 600/411 |
| 2015/0196222 A1 | 7/2015 | Stehning et al. | |
| 2015/0196266 A1* | 7/2015 | Fenchel | A61B 5/055 600/411 |

OTHER PUBLICATIONS

Kartmann, René et al. Integrated PET/MR imaging: Automatic attenuation correction of flexible RF coils. Medical Physics, vol. 40, No. 8, Aug. 2013.

D L Bailey, Transmission scanning in emission tomography, European journal of nuclear medicine and molecular imaging, 25(7): 774-787 (1998).

C. Burger et al., PET attenuation coefficients from CT images: experimental evaluation of the transformation of CT into PET 511-keV attenuation coefficients, European Journal of Nuclear Medicine 29(7): 922-927(2002).

\* cited by examiner

620

SYSTEM AND METHOD FOR ATTENUATION CORRECTION

CROSS-REFERENCE TO RELATED APPLICATIONS

This application is a continuation application of International Application No. PCT/CN2017/073449, filed on Feb. 14, 2017, to which this application claims priority. The disclosure of the above-referenced application is expressly incorporated herein by reference to its entirety.

TECHNICAL FIELD

This present disclosure relates to an imaging system, and more particularly, relates to a multi-modality imaging system.

BACKGROUND

Magnetic resonance imaging (MRI) is a non-invasive imaging technique that employs a powerful magnet to align the nuclei of atoms inside a target body, and a variable magnetic field that causes the atoms to resonate, a phenomenon called nuclear magnetic resonance. MRI may generate images with high resolution on soft tissues including, for example, urinary bladder, rectum, uterus, bone, articulation, muscle, etc. Positron emission tomography (PET) is a functional imaging technique that detects pairs of gamma rays emitted by a positron emitting radionuclide or a tracer. PET may be adopted to investigate metabolic process of a target body and used widely in field including, for example, oncology, neurology, psychiatry, cardiology, infectious diseases, musculo-skeletal imaging, etc. Positron emission tomography-magnetic resonance imaging (PET-MRI) is a hybrid imaging technique that utilizes the benefits of both PET and MRI. However, radio-frequency coils used for MRI process may cause attenuation of gamma rays in PET process.

SUMMARY

In one aspect of the present disclosure, a system is provided. The system includes a coil module and the coil module includes a flexible coil and a supporter. The supporter may be configured to hold the flexible coil. The flexible coil may be deformed to form a receiving space.

In another aspect of the present disclosure, a method is provided. The method includes generating an AC map of a coil module and an AC map of a bed; generating an AC map of a target body; generating a final AC map by inserting the AC maps of the coil module and the bed into the AC map of the target body; and correcting an image according to the final AC map.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

Figure 1:
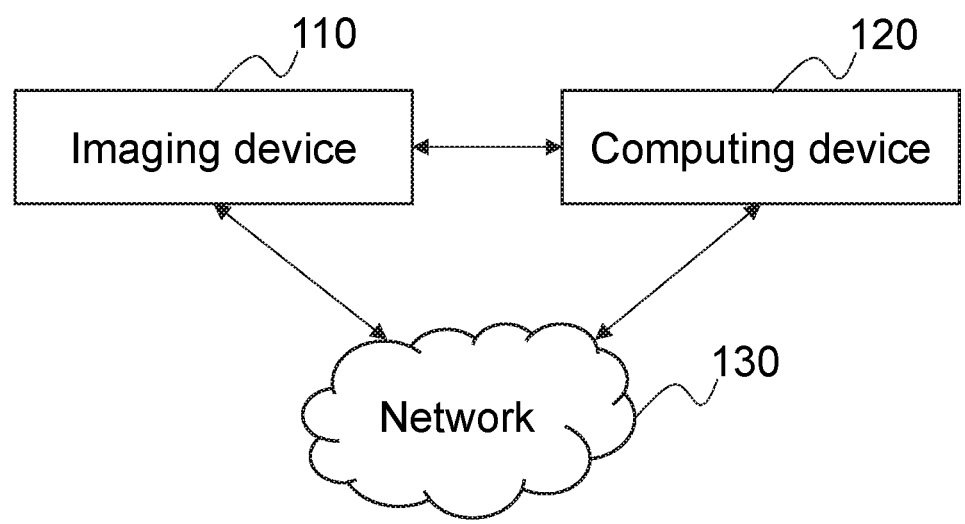
FIG. 1 is a block diagram of an exemplary imaging system according to some embodiments of the present disclosure.

In the following detailed description, numerous specific details are set forth by way of example in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

It will be understood that the term "system," "device," "apparatus," "module," "unit," and/or "block" used herein are one exemplary method to distinguish different components, elements, parts, sections or assemblies of different levels in ascending order. However, the terms may be exchanged or displaced by other expressions if they may achieve the same purpose.

It will be understood that when a device, apparatus, module, unit, component or block is referred to as being "on," "connected to," or "coupled to" another device, module, unit, or block, it may be directly on, connected or coupled to, or communicate with the other device, apparatus, module, unit, component or block, or an intervening device, apparatus, module, unit, component, or block may be present, unless the context clearly indicates otherwise. As used herein, the term "and/or" includes any and all combinations of one or more of the associated listed items.

The terminology used herein is for the purposes of describing particular examples and embodiments only, and is not intended to be limiting. As used herein, the singular forms "a," "an," and "the" may be intended to include the plural forms as well, unless the context clearly indicates otherwise. It will be further understood that the terms "include," and/or "comprise," when used in the present disclosure, specify the presence of integers, devices, behaviors, stated features, steps, elements, operations, and/or components, but do not exclude the presence or addition of one or more other integers, devices, behaviors, features, steps, elements, operations, components, and/or groups thereof. It will be further understood that the terms "construction" and "reconstruction," when used in this disclosure, may represent a similar process in which an image may be transformed from data.

The present disclosure may be implemented in a medical instrument including, for example, an imaging system, a therapy system, etc. The imaging system may be used to create a visual image of the internal structures of a target body for analysis, diagnosis, and/or therapy. The therapy system may be used to treat diseases. Merely by way of example, the therapy system may be an MRI guided radio-therapy system (e.g., an MRI-Linac system for real time radiotherapy treatment, an MRI guided high intensity focused ultrasound for tumor ablation, etc.). For illustration purposes, an imaging system may be described as an example below.

FIG. 1 is a diagram of an exemplary imaging system 100 according to some embodiments of the present disclosure. The imaging system 100 may be a single modality imaging system including, for example, a digital subtraction angiography (DSA) system, a magnetic resonance imaging (MRI) system, a computed tomography angiography (CTA) system, a positron emission tomography (PET) system, a single photon emission computed tomography (SPECT) system, a computed tomography (CT) system, a digital radiography (DR) system, etc. In some embodiments, the imaging system 100 may be a multi-modality imaging system including, for example, a positron emission tomography-computed tomography (PET-CT) system, a positron emission tomography-magnetic resonance imaging (PET-MRI) system, a single photon emission computed tomography-positron emission tomography (SPECT-PET) system, a digital subtraction angiography-magnetic resonance imaging (DSA-MRI) system, etc. For better understanding the present disclosure, a PET-MRI system may be described as an example of the imaging system 100. It should be noted that the imaging system 100 described below is merely provided for illustration purposes, and not intended to limit the scope of the present disclosure.

As illustrated in FIG. 1, in some embodiments, the imaging system 100 may include an imaging device 110, a computing device 120, and a network 130. The imaging device 110 may be configured to scan a target body to collect data of the target body. The target body may be a substance, a cell, a tissue, an organ, a part of or a whole body of a human being or an animal. For example, the target body may include brain, brain-stem, an organ, neck, spinal column, heart, breast, abdomen, muscle, skeleton, joint, soft tissue, liver, pancreas, bile ducts, or the like, or any combination thereof. Other exemplary target body may include a man-made composition of organic and/or inorganic matter.

The computing device 120 may be configured to process the data collected by the imaging device 110 to generate one or more images of the target body. In some embodiments, the computing device 120 may perform operations including, for example, data processing, parameters determining, attenuation correction (AC) map generating, image reconstructing, image correcting, image displaying, etc.

The network 130 may be configured to facilitate communications between components of the image system 100. In some embodiments, the network 130 may adopt communication techniques including, for example, wired network, wireless network, or Ethernet that assists transmitting and receiving data. In some embodiments, the network 130 may be a nanoscale network, a near field communication (NFC), a body area network (BAN), a personal area network (PAN, e.g., a Bluetooth, a Z-Wave, a Zigbee, a wireless USB), a near-me area network (NAN), a local wireless network, a backbone, a metropolitan area network (MAN), a wide area network (WAN), an internet area network (IAN, or cloud), or the like, or any combination thereof.

In some embodiments, the imaging device 110, the computing device 120, and/or the network 130 may be connected to or communicate with each other directly or indirectly. In some embodiments, the imaging device 110, the computing device 120, and the network 130 may be located adjacent to each other, for example, they may be integrated as one device. In other embodiments, one or more of the above components may be remote from each other. For example, the computing device 120 may be implemented on a cloud platform (e.g., a cloud computing platform or a cloud storing platform). As another example, the computing device 120 may be operated by a remote system, e.g., a remote medical system, a mobile medical system, a family medical system, or a remote security system.

Figure 2:
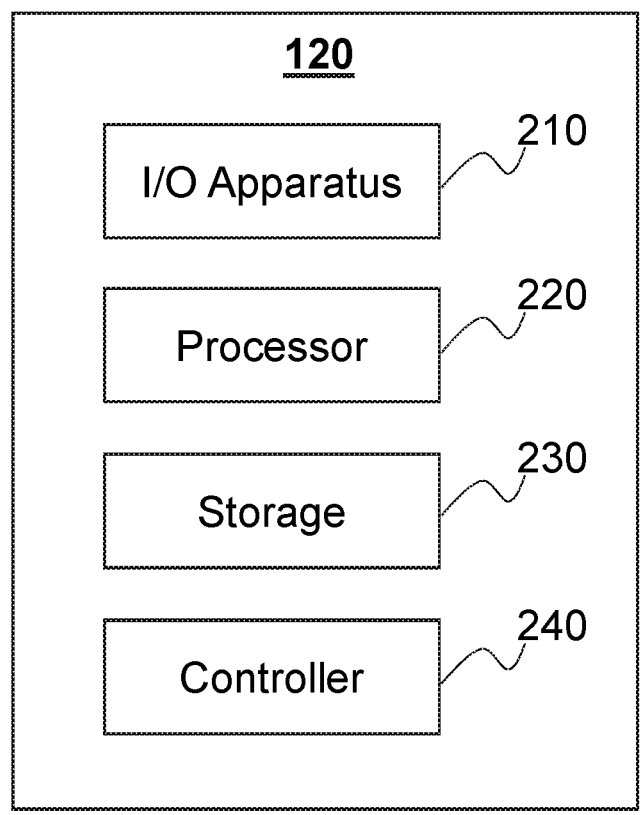
FIG. 2 is a block diagram of an exemplary computing device according to some embodiments of the present disclosure.

FIG. 2 is a block diagram of an exemplary computing device according to some embodiments of the present disclosure. The computing device 120 may be configured to process data acquired by the imaging device 110 to generate one or more images of target body. Term data used herein may be any information including, for example, number, text, voice, image, video, parameter, code, formula, file, algorithm, program, or the like, or any combination thereof. In some embodiments, the computing device 120 may include a computer, a computing machine, a data processor, an electronic computer, an information system, a work station, an intelligent terminal (e.g., a mobile phone or a wearable device), etc. As illustrated in FIG. 2, in some embodiments, the computing device 120 may include an input/output (I/O) apparatus 210, a processor 220, a storage 230, and a controller 240.

The I/O apparatus 210 may be configured to receive data and/or output data. For example, the I/O apparatus 210 may acquire data from the imaging device 110, the computing device 120, the network 130, or a user. Term user used herein may include an operator, a doctor, a patient, a robot, etc. In some embodiments, the I/O apparatus 210 may include a keyboard, a mouse, a camera, a microphone, a scanner, a display, a touch screen, or the like, or any combination thereof. In some embodiments, the I/O apparatus 210 may be configured to display data and/or supply a user interface. Term data used herein may be any information including, for example, number, text, voice, image, video, parameter, code, formula, file, algorithm, program, or the like, or any combination thereof. User interface may supply medium for user interaction with the computing device 120, for example, image viewing, parameter setting, position adjusting, process controlling, or the like, or any combination thereof. In some embodiments, display may include a liquid crystal display (LCD), a light emitting diode (LED) based display, a flat panel display or curved screen, a cathode ray tube (CRT), a 3D display (e.g., a virtual reality display), a plasma display panel, or the like, or any combination thereof.

The processor 220 may be configured to execute one or more instructions stored in a storage device (e.g., the storage 230), and, when executing the instruction(s), the processor 220 may perform functions in accordance with techniques described herein. In some embodiments, the processor 220 may perform functions including, for example, positon controlling, data processing, image reconstruction, attenuation correction (AC) map generating, image correcting, or the like, or any combination thereof. For example, position of target body and/or components of the imaging device 110 may be controlled by the processor 220. As another example, attenuation caused in imaging process may be corrected by the processor 220. In some embodiments, the processor 220 may include any processor-based unit. Merely by way of example, the processor may include a microcontroller, a reduced instruction set computer (RISC), application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an acorn reduced instruction set computing (RISC) machine (ARM), or any other circuit or processor capable of executing the functions described herein, or the like, or any combination thereof.

The storage 230 may be configured to store the instructions to be executed by the processor 210. The storage 230 may also be configured to store data acquired from the imaging device 110, the computing device 120, the network 130, or the user. Term data used herein may be any information including, for example, number, text, voice, image, video, parameter, code, formula, file, algorithm, program, or the like, or any combination thereof. For example, parameter of the coil 510 and/or the supporter 520 may be determined and stored in the storage 230. As another example, AC map generated by the processor 220 may be stored in the storage 230. In some embodiments, the storage 230 may be a device storing data by electricity, magnetism or light. For example, the storage 230 may include a Random Access Memory (RAM), a Read Only Memory (ROM), a hard disk, a magnetic disk, a USB disk, a CD, a DVD, or the like, or any combination thereof.

The controller 240 may be configured to control one or more components of the imaging system 100 based on one or more instructions received from the processor 210. For example, the controller 240 may interpret an operation code and/or a synthetic address code of an instruction. As another example, the controller 240 may transmit control signal to relative component of the computing device 120. In some embodiments, the controller 240 may include a program counter, an instruction register, a sequence control element, and/or a combinational logic circuit.

It should be noted that the above description about the computing device 120 is merely provided for the purposes of illustration, and not intended to limit the scope of the present disclosure. For persons having ordinary skills in the art, multiple variations and modifications may be made under the teachings of the present disclosure. In some embodiments, some components in the computing device 120 may be eliminated, integrated into one component, or displaced by other component. For example, the processor 220 and the controller 240 may be integrated together. As another example, I/O apparatus may be disintegrated into an input module and/or an output module. For still another example, the processor 220 and/or the storage 230 may be displaced by a cloud platform (e.g., a cloud computing platform or a cloud storing platform). However, those variations and modifications do not depart from the scope of the present disclosure.

Figure 3:
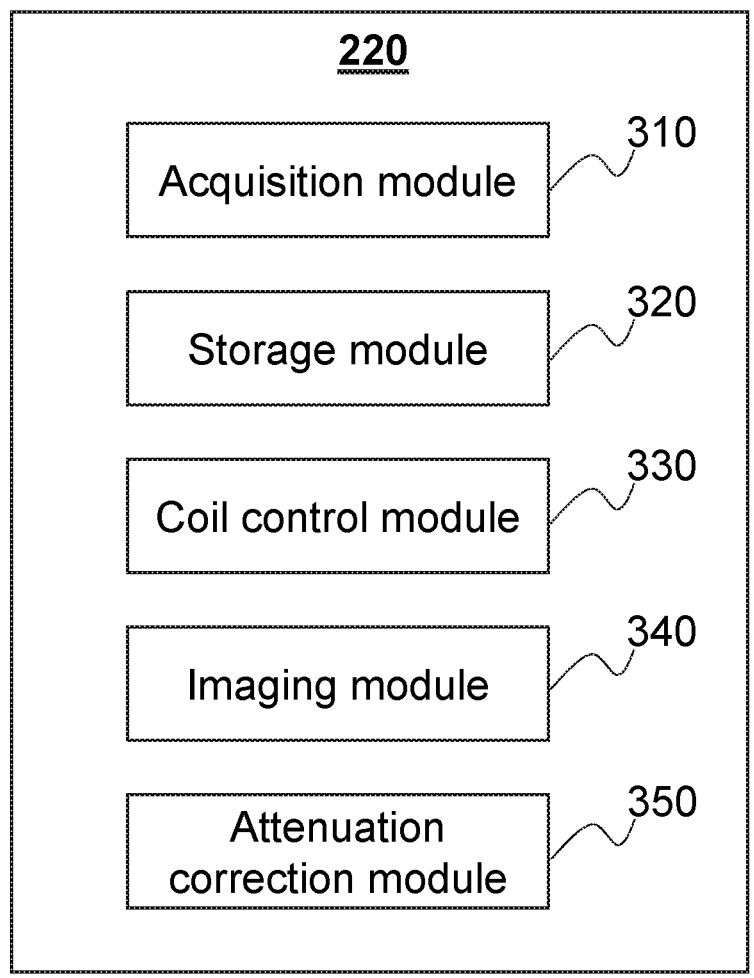
FIG. 3 is a block diagram of an exemplary processor according to some embodiments of the present disclosure.

FIG. 3 is a block diagram of an exemplary processor according to some embodiments of the present disclosure. It should be noted that processor illustrated in FIG. 3 may merely be an exemplary embodiment of the processor 220 in FIG. 2, and not intended to limit the scope of the present disclosure. As illustrated in FIG. 3, the processor 220 may include an acquisition module 310, a storage module 320, a coil control module 330, an imaging module 340, and an attenuation correction module 350. Generally, the word "module" as used herein, refers to logic embodied in hardware or firmware, or to a collection of software instructions. The modules described herein may be implemented as software and/or hardware modules and may be stored in any type of non-transitory computer-readable medium or other storage device. In some embodiments, a software module may be compiled and linked into an executable program. It will be appreciated that software modules can be callable from other modules or from themselves, and/or can be invoked in response to detected events or interrupts. Software modules configured for execution on computing devices (e.g., the processor 210) can be provided on a computer readable medium, such as a compact disc, a digital video disc, a flash drive, a magnetic disc, or any other tangible medium, or as a digital download (and can be originally stored in a compressed or installable format that requires installation, decompression, or decryption prior to execution). Such software code can be stored, partially or fully, on a memory device of the executing computing device, for execution by the computing device. Software instructions can be embedded in a firmware, such as an EPROM. It will be further appreciated that hardware modules can be included of connected logic units, such as gates and flip-flops, and/or can be included of programmable units, such as programmable gate arrays or processors. The modules or computing device functionality described herein are preferably implemented as software modules, but can be represented in hardware or firmware. In general, the modules described herein refer to logical modules that can be combined with other modules or divided into sub-modules despite their physical organization or storage.

The acquisition module 310 may be configured to receive data from, for example, the imaging device 110, the computing device 120, the user, and/or other modules of the processor 220. Term user used herein may include an operator, a doctor, a patient, a robot, etc. For example, a user may input information of the coil module 430 and/or the bed 420. In some embodiments, function of the acquisition module 310 may be performed by the I/O apparatus 210 as shown in FIG. 2. The storage module 320 may be configured to store data from, for example, the imaging device 110, the computing device 120, the user, and/or other modules of the processor 220. In some embodiments, function of the storage module 320 may be performed by the storage 230 as shown in FIG. 2.

Figure 4:
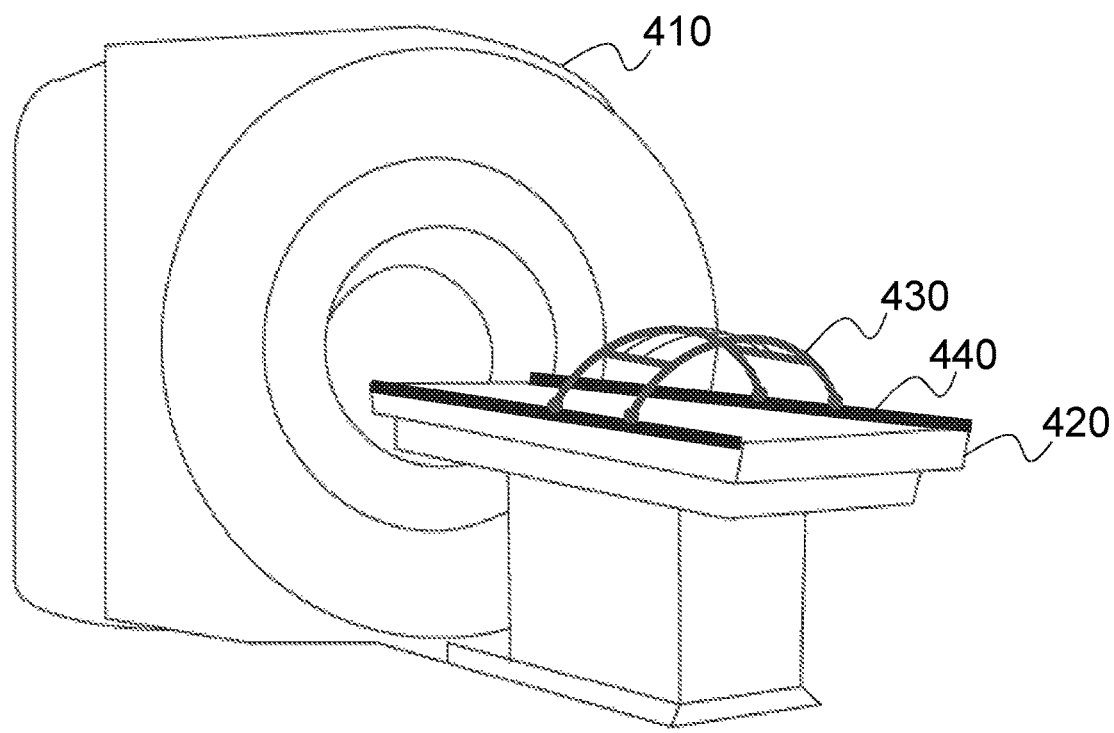
FIG. 4 is a graph of an exemplary imaging device according to some embodiments of the present disclosure.

Coil control module 330 may be configured to control the coil module 430 as shown in FIG. 4. In some embodiments, function of the coil control module 330 may be performed by the controller 240 as shown in FIG. 2. For example, the coil control module 330 may control type, structure, and/or movement strategy of the coil module 430. Type of the coil module 430 may indicate a category of volume coil or surface coil used for different target body including, for example, brain, brain-stem, an organ, neck, spinal column, heart, breast, muscle, skeleton, joint, soft tissue, liver, pancreas, bile ducts, or the like, or any combination thereof. Structure of the coil module 430 may include size, shape, and/or assembly method of the coil module 430. Movement strategy of the coil module 430 may include, for example, starting position, speed, direction, and/or stopping position of the coil module 430. In some embodiments, different coils may have their own pre-determined AC maps, AC map generating methods, and/or movement strategies. The coil control module 330 may be configured to identify a coil and match a pre-determined AC map, an AC map generating method, and/or a movement strategy to the coil.

The imaging module 340 may be configured to generate an image. Image generated may be a 2D or 3D image including, for example, a PET image, a CT image, a fusing image, or the like, or any combination thereof. In some embodiments, the imaging module 340 may generate an image through parameter setting, data preprocessing, image reconstructing, and/or image fusion. In some embodiments, the imaging module 340 may employ image reconstruction techniques including, for example, Fourier reconstruction (FR), constrained image reconstruction (CIR), regularized image reconstruction (RIR), filtered back-projection (FBP) reconstruction, maximum-liked expectation-maximization (MLEM) reconstruction, or the like, or a modification thereof, or any combination thereof.

The attenuation correction module 350 may be configured to correct attenuation of an image. In some embodiments, attenuation may be caused by a target body and/or a fixed component of the imaging device 110. The fixed component may be the coil module 430 and/or the bed 420. For example, the coil module 430 may lead to photon attenuation during PET scanning process in a PET-MRI system. In some embodiments, the attenuation correction module 350 may perform correction according to AC maps of the target body and/or the fixed component of the imaging device 110. The AC maps may be determined before, during, and/or after scanning process. For example, the AC maps of the coil module 430 and/or the bed 420 may be predetermined and stored in the storage 230 or the storage module 320 in advance through a transmission scanning method, a simulation method, or a combination thereof. As another example, AC map of the target body may be generated according to an MR image and/or PET image acquired after scanning of the target body. The transmission scanning method may include generating an AC map through a CT image, an MR image, and/or a PET image. The simulation method may include determining an AC map based on the properties of the coil module 430 and/or the bed 420.

It should be noted that the above description about the processor 220 is merely provided for the purposes of illustration, and not intended to limit the scope of the present disclosure. For persons having ordinary skills in the art, multiple variations and modifications may be made under the teachings of the present disclosure. In some embodiments, some components in the processor 220 may be eliminated, integrated into one component, or displaced by other component. For example, the acquisition module 310 and/or the storage module 320 may be eliminated. As another example, the imaging module 340 and the attenuation correction module 350 may be integrated into one module. However, those variations and modifications do not depart from the scope of the present disclosure.

FIG. 4 is a graph of an exemplary imaging device according to some embodiments of the present disclosure. The imaging device 110 may be configured to collect data of target body. As illustrated in FIG. 4, an exemplary imaging device 110 may include a scanner 410, a bed 420, a coil module 430, and a rail 440. The scanner 410 may be configured to scan a target body. In some embodiments, the scanner 410 may be a single modality scanner or a multi-modality scanner that used in the imaging system 100 as illustrated in FIG. 1. For better understanding the present disclosure, a PET-MRI scanner may be described as an example of the scanner 410. PET-MRI scanner may include a magnet to create a main magnetic field, a gradient coil to create a gradient field, a PET detector to collect photon, etc. The bed 420 may be configured to support a target body when been scanned in the scanner 410. In some embodiments, height and/or movement strategy of the bed 420 may be adjusted by the controller 240. The coil module 430 may be configured to capture a magnetic resonance signal generated by the target body. The rail 440 may be configured to guide the movement of the coil module 430. For example, for the coil module 430 employed in breast and/or abdomen scanning, the rail 440 may assist to execute movement strategy including, for example, starting position, speed, direction, and/or stopping position of the coil module 430. In some embodiments, the rail 440 may be optional.

Figure 5:
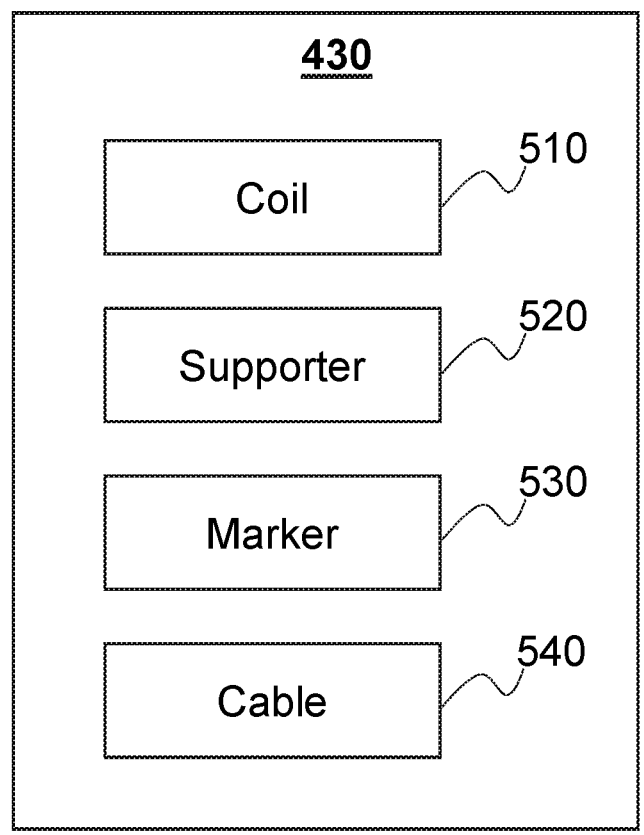
FIG. 5 is a block diagram of an exemplary coil module according to some embodiments of the present disclosure.

FIG. 5 is a block diagram of an exemplary coil module according to some embodiments of the present disclosure. As illustrated in FIG. 5, the coil module 430 may include a coil 510, a supporter 520, a marker 530, and a cable 540. In some embodiments, the marker 530 and/or the cable 540 may be optional.

The coil 510 may be a main coil, a shim coil, a gradient coil, a radiofrequency (RF) coil, or the like, or any combination thereof. For better understanding the present disclosure, an RF coil may be described as an example of the coil 510. In some embodiments, the RF coil may serve as a transmitter, a receiver, or both. When used as a transmitter, the RF coil may generate an oscillating/rotating magnetic field that is perpendicular to the static main magnetic field. When used as a receiver, the RF coil may detect a magnetic resonance signal. In some embodiments, the RF coil may be a volume coil or a surface coil. Volume coil may be configured to provide a homogeneous RF excitation across a large volume of a target body. Surface coil may be configured to provide an RF excitation over a small region of interest (ROI) of target body. In some embodiments, amount, type, shape, and/or structure of the coil 510 may vary according to different scenarios in the present disclosure. Exemplary shape and/or structure of the coil 510 may be illustrated in connection with FIG. 9 as described elsewhere in this disclosure.

The supporter 520 may be configured to hold the coil 510 and keep the coil 510 in a stationary status. In some embodiments, in order to be suitable for diversity of target bodies, the supporter 520 may be prefabricated with different shapes, sizes, and/or materials. Shapes of the supporter 520 may include a circle, an arc, a flat, a cylinder, a cubic, a cuboid, a sphere, an irregular shape, or the like, or any combination thereof. Sizes of the supporter 520 may include small, medium, large, extra-large, etc. In some embodiments, shape and/or size of the supporter 520 may be adjustable. Material of the supporter 520 may include plastic or a composite. Exemplary plastic may include polyethylene, polystyrene, polymethyl methacrylate, polyvinyl chloride, polyamide, polyester, or the like, or any combination thereof. Exemplary composite may include a matrix and a reinforcement phase. In some embodiments, the matrix may be organic, for example, polycarbonate. Reinforcement phase may be a glass fiber, a quartz fiber, a carbon fiber, a silicon carbide fiber, an aluminum oxide fiber, a boron fiber, a boron nitride fiber, a silicon carbide particle, a titanium carbide particle, a boron carbide particle, an aluminum oxide particle, a silicon nitride particle, a boron nitride particle, a graphite particle, or the like, or any combination thereof. Exemplary shape and/or structure of the supporter 520 may be illustrated in connection with FIG. 10 as described elsewhere in this disclosure.

The marker 530 may be configured to indicate a position of the coil module 430. The marker 530 may be attached on the coil 510 and/or the supporter 520. In some embodiments of attenuation correction, an AC map of the coil module 430 may be inserted into or registered with an AC map of a target body. The marker 530 may be visible in both the AC map of target body (e.g., generated through an MR image, a CT image, a PET image, etc.) and the AC map of the coil module 430 (e.g., generated through an MR image, a CT image, a PET image, a simulation, etc.), and the marker 530 may be configured to indicate the positions of the target body and the coil module 430. In some embodiments, if the supporter 520 becomes rigid (e.g., in a rigid state), the marker 530 on the supporter 520 may also be stable. Accordingly, the registering between AC map of coil module and AC map of the target body may be a rigid registration. In some embodiments, the marker 530 may also be optional.

The cable 540 may be configured to connect the coil module 430 with the imaging system 100. The cable 540 may be made by a wire and configured to transmit energy, instruction, data, or other information between the coil module 430 and the imaging system 100. In some embodiments, the cable 540 may be optional. For example, the cable 540 may be replaced by a wireless communication device. The wireless communication device may be connected to the imaging system 110 via, for example, the network 130 using communication techniques as described elsewhere in this disclosure.

It should be noted that the above description about the coil module 430 is merely provided for the purposes of illustration, and not intended to limit the scope of the present disclosure. For persons having ordinary skills in the art, multiple variations and modifications may be made under the teachings of the present disclosure. For example, the marker 530 and/or the cable 540 may be optional in some embodiments. As another example, there may be other components in the coil module 430. Merely by way of example, the coil module 430 may also have a connect part that assists the coil module 430 to be connected with the rail 440 in FIG. 4. However, those variations and modifications do not depart from the scope of the present disclosure.

Figure 6:
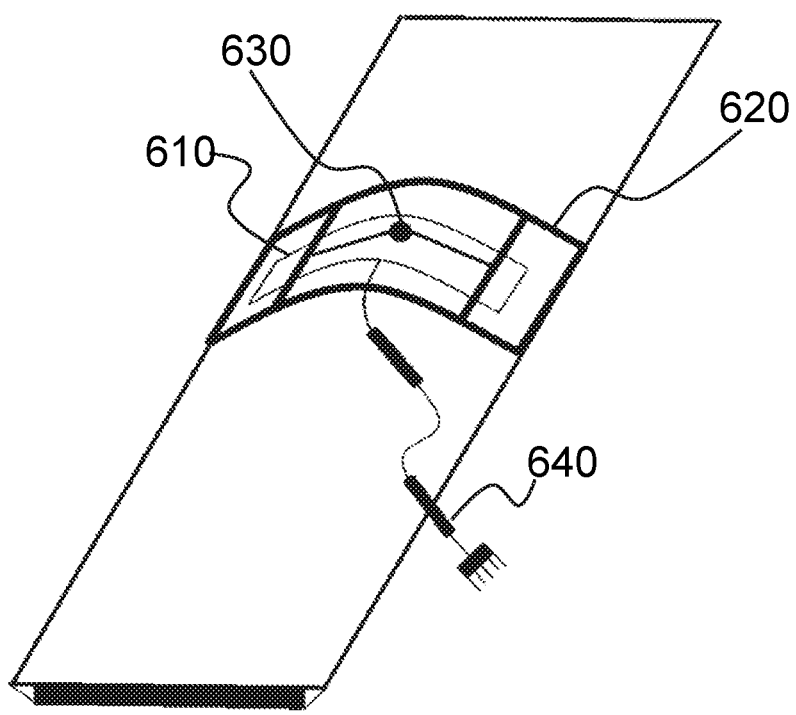
FIG. 6 is a graph of an exemplary coil module according to some embodiments of the present disclosure.

FIG. 6 is a graph of an exemplary coil module according to some embodiments of the present disclosure. It should be noted that the coil module 600 in FIG. 6 is merely an example of the coil module 430, and not intended to limit the scope of the present disclosure. As illustrated in FIG. 6, the coil module 600 may include a coil 610, a supporter 620, a marker 630, and a cable 640. The coil 610 may merely be an example of the coil 510, and variations or modifications may be allowed in the present disclosure. For illustration purposes, the coil 610 may be a flexible coil used for breast and/or abdomen scanning. The coil 610 may be employed as a volume coil or a surface coil. The shape of the coil 610 may be an arc for containing a target body. In some embodiments, the shape and/or size of the coil 610 may be determined by the shape and/or size of the supporter 620. In some embodiments, the coil 610 may include other components.

Figure 7A:
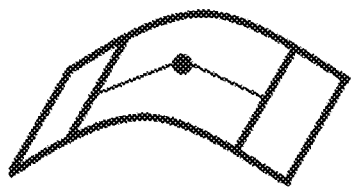
FIGS. 7A-7C illustrate an exemplary supporter according to some embodiments of the present disclosure.
Figure 7B:
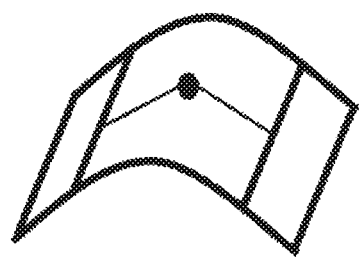
Figure 7C:
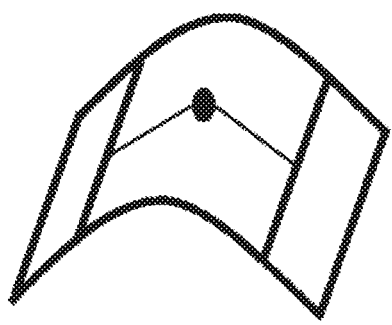

The supporter 620 may be configured to hold the coil 610. The supporter 620 may merely be an example of the supporter 520, and variations or modifications may be allowed in the present disclosure. The supporter 620 may be prefabricated with different shapes, sizes, and/or materials. As shown in FIG. 6, the shape of the supporter 620 may be an arc for containing a target body. In some embodiments, size of the supporter 620 may be adjustable. For example, the supporter 620 may include an adjustable component (not shown in FIG. 6) to change the size of the supporter 620. Adjustable component may change the size of the supporter 620 in a continuous manner or in a discrete manner. For the continuous manner, size of the supporter 620 may increase or decrease continually according to the size of target body. For the discrete manner, size of the supporter 620 may be changed between a plurality of predetermined sizes including, for example, small, medium, large, extra-large, etc. In some embodiments, size of the supporter 620 may be definite, then a series of the supporters 620 with different sizes may be manufactured to fit different sized target body. As illustrated in FIGS. 7A-7C, the supporter 620 may have three sizes including, for example, small size in FIG. 7A, medium size in FIG. 7B, and large size in FIG. 7C. In some embodiments, the supporter 620 may reach a rigid state when its structures and shapes are fixed. The supporter 620 may have different rigid states through adjusting its structures and/or shapes according to methods described elsewhere in the present disclosure. Term rigid used herein may indicate a state of the supporter 620 that not able to be deformed easily. Materials of the supporter 620 may include plastic or a composite same as the materials of the supporter 520. Merely by way of example, the supporter 620 may be made of polyamide or a glass fiber reinforced polycarbonate composite.

In some embodiments, the coil 610 and the supporter 620 may be connected with each other in a non-detachable or in a detachable way. For the non-detachable connecting way, the coil 610 may be fixed to the supporter 620 through gluing, welding, riveting, pressing, casting, or the like, or any combination thereof. For the detachable connecting way, the coil 610 may be fixed to the supporter 620 through screw connection, pinning, elastic deformation, buttoning, tying, sticking, clasping, plugging, or the like, or any combination thereof. Merely by way of example, in case of plugging connection, there may be a first fixture in the coil 610 and a second fixture in the supporter 620 (first fixture and second fixture are not shown in FIG. 6). When first fixture is plugged in second fixture (or second fixture is plugged in first fixture), the coil 610 and the supporter 620 may be connected with together.

The marker 630 may be an example of the marker 530, and variations or modifications may be allowed in the present disclosure. The number of the marker 630 may be one or more. The marker 630 may be attached to a place on the coil 610 and/or the supporter 620. The place on the coil 610 and/or the supporter 620 may include, for example, top, bottom, left, right, middle, surrounding, or the like, or any combination thereof. In some embodiments of containing two or more markers 630, the markers 630 may be arranged arbitrarily.

The cable 640 may be an example of the cable 540, and variations or modifications may be allowed in the present disclosure. In some embodiments, the cable 640 may be optional. For example, the cable 640 may be replaced by a wireless communication device configured to perform the similar functions as the cable 640 disclosed in this application. The wireless communication device may be connected to the imaging system 110 via, for example, the network 130 using communication techniques as described elsewhere in this disclosure.

It should be noted that the above description about the coil module 600 is merely provided for the purposes of illustration, and not intended to limit the scope of the present disclosure. For persons having ordinary skills in the art, multiple variations and modifications may be made under the teachings of the present disclosure. For example, the shape and/or size of the supporter 620 may be changed. As another example, the position of the cable 640 may be moved to other place on the coil 610. As still another example, the marker 630 and/or the cable 640 may be optional. However, those variations and modifications do not depart from the scope of the present disclosure.

Figure 8:
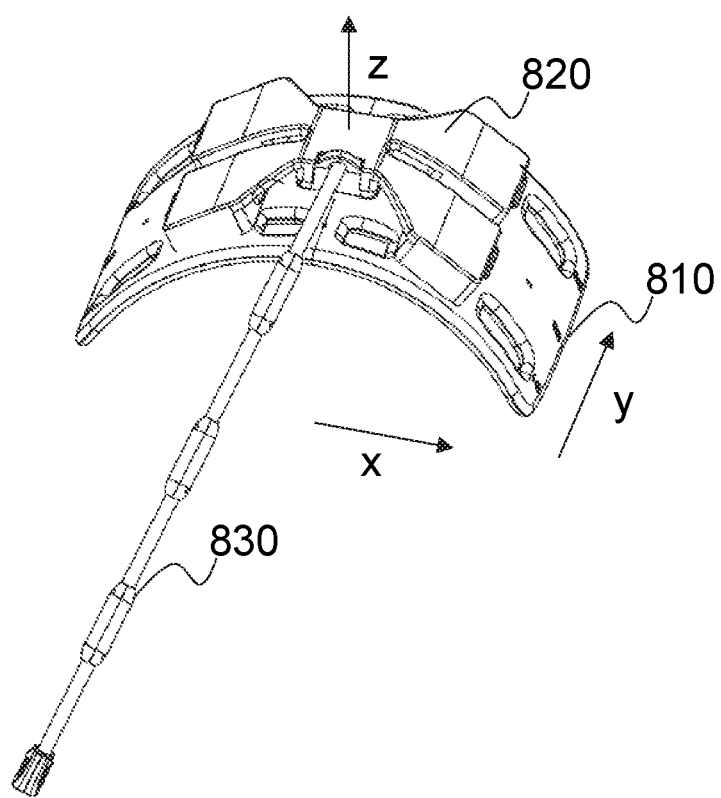
FIG. 8 is a graph of an exemplary coil module according to some embodiments of the present disclosure.

FIG. 8 illustrates an exemplary coil module according to some embodiments of the present disclosure. It should be noted that the coil module 800 in FIG. 8 is merely an example of the coil module 430, and not intended to limit the scope of the present disclosure. As illustrated in FIG. 8, the coil module 800 may include a coil 810, a supporter 820, and a cable 830. The supporter 820 may hold the coil 810 through clasping. The coil 810 may merely be an example of the coil 510, and variations or modifications may be allowed in the present disclosure. The supporter 820 may merely be an example of the supporter 520, and variations or modifications may be allowed in the present disclosure.

Figure 9:
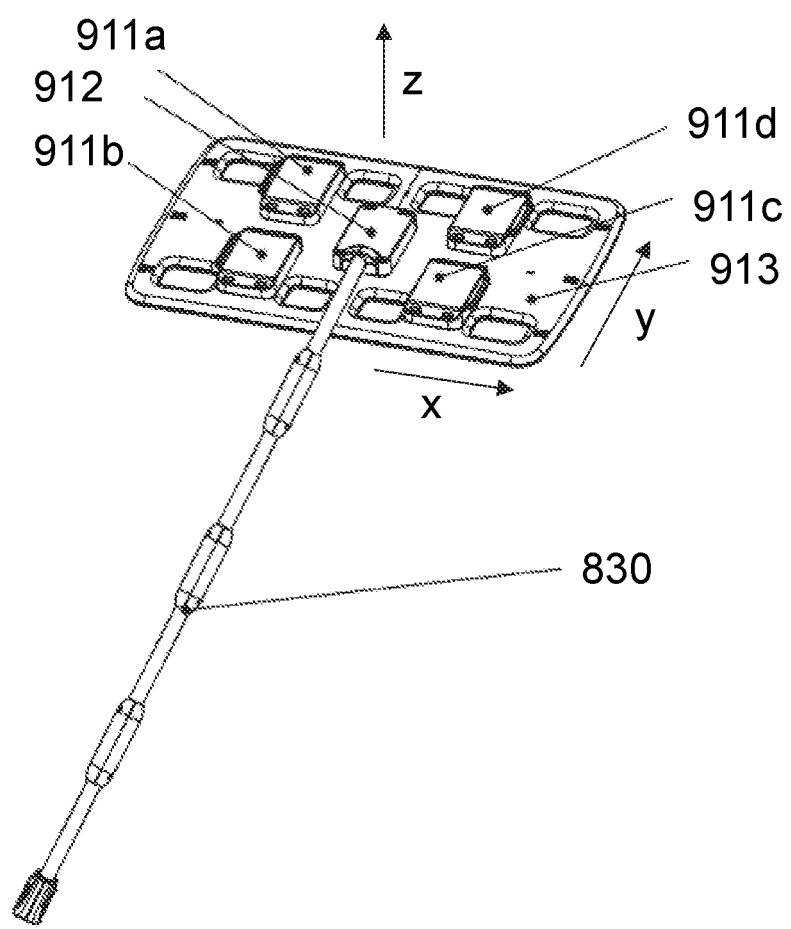
FIG. 9 is a graph of an exemplary coil according to some embodiments of the present disclosure.

Merely by way of example, FIG. 9 shows an exemplary coil 810 according to some embodiments of the present disclosure. The coil 810 may be a flexible coil used for breast and/or abdomen scanning. The coil 810 may include a first fixture, a package 913, and a cable 830. In some embodiments, the first fixture may include one or more coil units contained in boxes arranged in an array. As illustrated in FIG. 9, the first fixture may include side coil boxes (including, for example, side coil boxes 911a-911d) and a middle coil box 912. The side coil boxes 911a-911d and/or the middle coil box 912 may include a radio-frequency circuit board. In some embodiments, the side coil boxes 911a-911d may be located at the four corners of the coil 810 and form a 2×2 array. Other configurations of the side coil boxes are also contemplated, for example, a 1×2 array, a 2×3 array, a 2×4 array, etc. The middle coil box 912 may be located in the middle of the coil 810. For example, the middle coil box 912 may be at the crossing point of two imaginary lines from the side box 911a to the side box 911c and from the side box 911b to the side box 911d. In some embodiments, the middle coil box 912 may be connected with the imaging system 100 with the cable 830.

The package 913 may be configured to pack the first fixture. For example, the boxes containing coil units may be installed on the package 913. As illustrated in FIG. 9, the shape of the package 913 may be a rectangle in a plane determined by x axis and y axis. In some embodiments, the shape of the package 913 may be a square, a rounded rectangle, an ellipse, an irregular shape, etc. In some embodiments, the first fixture may be convex along z axis direction compared with the plane of the package 913 determined by the x axis and y axis. The package 913 may be made from flexible materials including, for example, rubber, plastic, and/or composite. The package 913 may be deformed under an external force. For example, it may be bent into an arc shape as shown in FIG. 8. In some embodiments, radian of the arc may be determined by the supporter 820.

Figure 10:
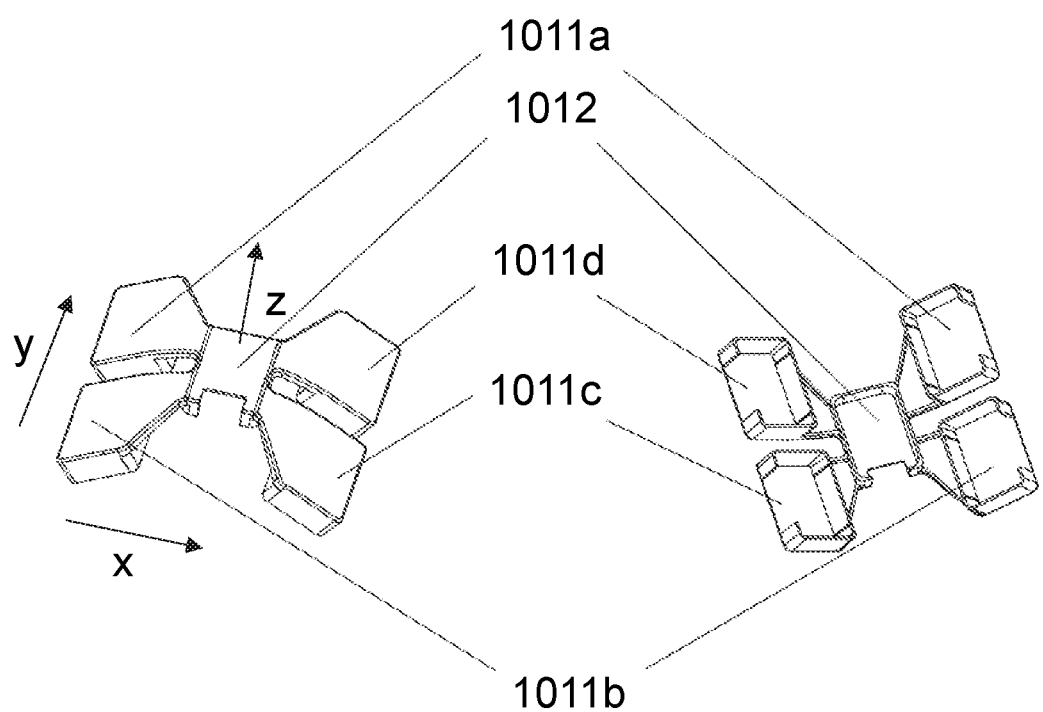
FIG. 10 is a graph of an exemplary supporter according to some embodiments of the present disclosure.

Merely by way of example, FIG. 10 shows an exemplary supporter 820 according to some embodiments of the present disclosure. The supporter 820 may include a second fixture. The second fixture may include side fixation boxes (including, for example, side fixation boxes 1011a-1011d) and a middle fixation box 1012. In some embodiments, the supporter 820 may include a base with curved surfaces. The side fixation boxes 1011a-1011d and the middle fixation box 1012 may be installed on the base. In some embodiments, the middle coil box 1012 may be located in the middle of the side fixation boxes 1011a-1011d. In some embodiments, the side fixation boxes 1101a-1101d and the middle fixation box 1012 may be in a same plane or different planes. In some embodiments, number, shape, and/or dimensions (e.g., length, width, and/or height) of the side fixation boxes 1011a-1011d and the middle fixation box 1012 may be adjusted according to specifications of coil 810 (e.g., a shape, structure, configuration, material thereof). For example, to be buttoned on the side coil box 911a-911d or the middle coil box 912, the side fixation boxes 1011a-1011d or the middle fixation box 1012 may have the length, width, and/or height that match with (or being bigger slightly than) the length, width, and/or height of the side coil boxes 911a-911d or the middle coil box 912, respectively. As another example, the size of the base may be adjusted. For example, the side fixation boxes 1011a-1011d and the middle fixation box 1012 may be connected by a collapsible component, and the dimensions of the supporter 820 may be adjusted by expanding or shortening the collapsible component.

In some embodiments, the supporter 820 may be adjusted to change the structure of the coil 810. For example, when angle between the surface determined by side fixation box 1011a, side fixation box 1011b, and middle fixation box 1012 and the surface determined by side fixation box 1011c, side fixation box 1011d, and middle fixation box 1012 are increased or decreased, the radian of the arc of the supporter 820 may be increased or decreased correspondingly. In some embodiments, the angle between the surface determined by side fixation box 1011a, side fixation box 1011b, and middle fixation box 1012 and the surface determined by side fixation box 1011c, side fixation box 1011d, and middle fixation box 1012 may be any value chosen from 0 degree to 180 degree. Preferably, the angle may be chosen from 30 degree to 150 degree. More preferably, the angle may be chosen from 60 degree to 120 degree. The supporter 820 may be made of the same material as the supporter 520. Merely by way of example, the supporter 820 may be made of polyamide or a glass fiber reinforced polycarbonate composite.

In some embodiments, the distance between the side fixation boxes 1011a and 1011b (or fixation boxes 1011c and 1011d) may be equal to the distance between the side coil fixation boxes 911a and 911b (or the coil fixation boxes 911c and 911d). The distance between the side fixation boxes 1011a and 1011d (or the side fixation boxes 1011b and 1011c) may be no greater than the distance between the side coil fixation boxes 911a and 911d (or the coil fixation boxes 911b and 911c). In some embodiments, as shown in FIG. 8, the coil 810 and the supporter 820 may be deformed into curved shapes (e.g., an arc, a camber, etc.) to fit the shape of the target body (e.g., breast, abdomen, etc.). In some embodiments, the shape of coil 810 may be predetermined according to the shape of the target body. To assemble the supporter 820 and the coil 810 together, the center angle corresponding to the arc between side fixation boxes 1011a and 1011d (or the side fixation boxes 1011b and 1011c) may be no greater than the center angle corresponding to the arc between the side coil fixation boxes 911a and 911d (or the side coil fixation boxes 911b and 911c) when the supporter 820 is substantially parallel with the coil 810. In some other embodiments, the supporter 820 and the coil 810 may be assembled together in advance, then the coil 810 may be adjusted to fit the shape of the target body by adjusting the base of the supporter 820.

Return to FIG. 8, in some embodiments, if the coil 810 and the supporter 820 is assembled together, a receiving space for containing a target body under the coil 810 may be generated. The receiving space may be open along y axis direction and z axis direction. The package 913 of the coil 810 may be located between the receiving space and the supporter 820, such that the coil 810 may be in a better contact with the target body without obstacle of the supporter 820. Such arrangement may improve noise-signal ratio and the quality of the image generated.

In some embodiments, the coil 810 may be fixed to the supporter 820 through a detachable way including, for example, screw connection, pinning, elastic deformation, buttoning, tying, sticking, clasping, plugging, or the like, or any combination thereof. Merely by way of example, in case of plugging connection, when the first fixture is plugged in the second fixture (or second fixture is plugged in first fixture), the coil 810 and the supporter 820 may be assembled together. In some embodiments, if the coil 810 and the supporter 820 is assembled together, there may be a gap between them, in other words, the coil 810 may be apart from the supporter 820.

It should be noted that the above description about the coil module 800 is merely provided for the purposes of illustration, and not intended to limit the scope of the present disclosure. For persons having ordinary skills in the art, multiple variations and modifications may be made under the teachings of the present disclosure. For example, the coil 810 may have two, three, four, or any number of side coil boxes. As another example, the number of side fixation boxes in the supporter 820 may be different from side coil boxes in the coil 810. As still another example, there may be a marker on the supporter 820. However, those variations and modifications do not depart from the scope of the present disclosure.

Figure 11:
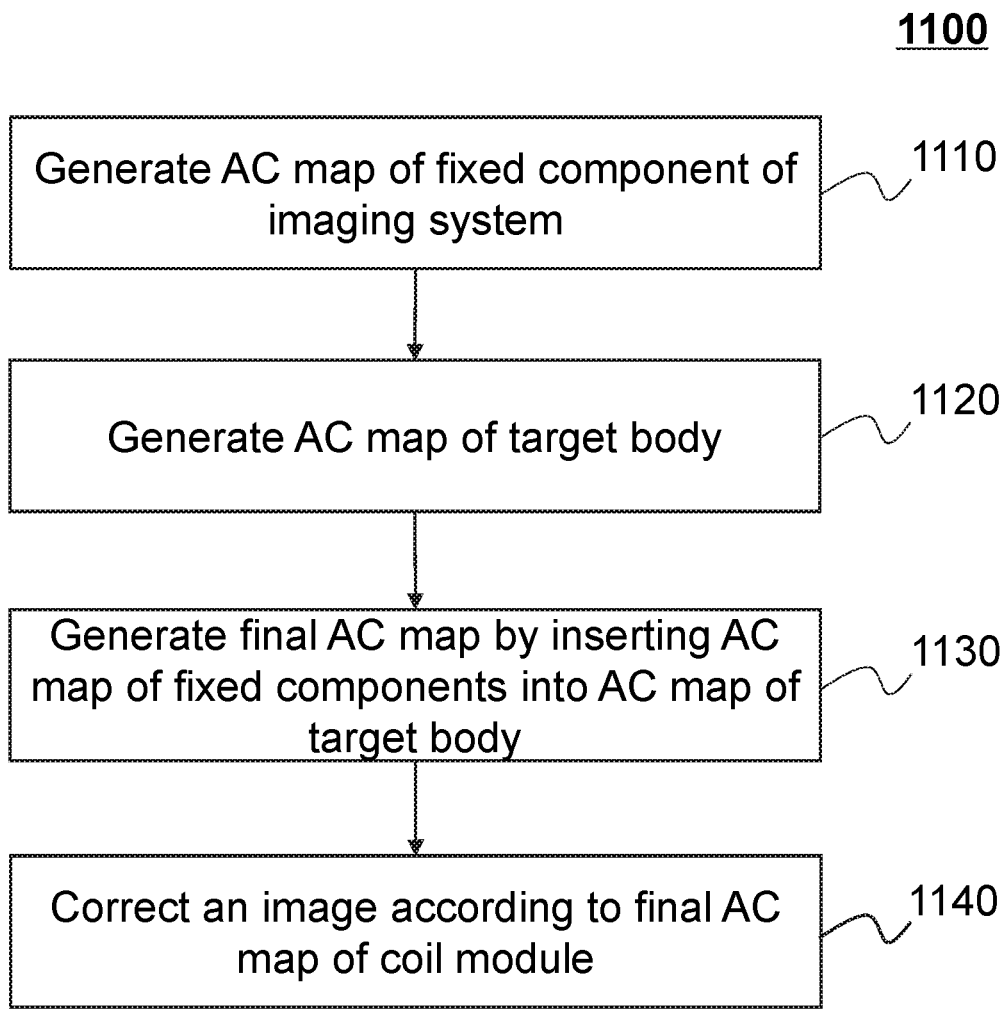
FIG. 11 is a flow chart of an exemplary imaging process according to some embodiments of the present disclosure.

FIG. 11 is a flow chart of an exemplary imaging process according to some embodiments of the present disclosure. In some embodiments, a process 1100 may be implemented in the imaging system 100 illustrated in FIG. 1. For example, step 1110, step 1120, and step 1140 may be implemented by the computing device 120.

In 1110, the processor 220 may generate an AC map of a fixed component. The fixed component may include the coil module 430, the bed 420, etc. The method for generating an AC map of the fixed component may include a transmission scanning method, a simulation method, or a combination thereof. The transmission scanning method may include generating an AC map based on a CT image, an MR image, and/or a PET image. The simulation method may include computing an AC map based on the properties of the coil module 430 and/or the bed 420. In some embodiments, the simulation method may be performed based on a method for generating an AC map of the coil module 430 in connection with FIG. 12 discussed as described elsewhere in this disclosure.

In 1210, the processor 220 may determine one or more parameters of the coil module 430. The parameters may include information relating to the coil module 430, including, for example, the material of the coil 510, structure of the coil 510, material of the supporter 520, structure of the supporter 520, material of the marker 530, structure of the marker 530, material of the cable 530, structure of the cable 530, or the like, or any combination thereof. Merely by way of example, the processor 220 may determine an attenuation coefficient of the material of the coil 510 or material of the supporter 520 according to the parameter of the coil module 430. The attenuation coefficient may indicate an intensity attenuation caused by absorbing materials passed through by photon (e.g., the material of the coil 510 and/or the supporter 520). Merely by way of example, the material of the coil 510 may include metal and/or absorbing materials that consists integrated circuit board. The material of the supporter 520 may include polyamide and/or a glass fiber reinforced polycarbonate composite. In some embodiments, the determination of the attenuation coefficient of different absorbing materials may depend on the properties of the absorbing materials. For example, if the absorbing material is known (e.g., polyamide, glass fiber, polycarbonate, or metal), the attenuation coefficient may be determined by simulation of Geant4 which is a platform for "the simulation of the passage of particles through matter," using Monte Carlo methods. In some embodiments, if the absorbing material is unknown (e.g., integrated circuit boards), the AC map of the coil module 430 including the integrated circuit boards may be generated according to the methods of transmission scanning described in *European journal of nuclear medicine and molecular imaging*, 1998, 25(7): 774-787. In some embodiments, domains of the known materials in the AC map generated by a transmission scanning may be replaced by the AC map generated based on a simulation.

When the parameters of the coil 510, the supporter 520, the marker 530, and/or the cable 540 are determined, the parameters may be stored in the storage module 320 and/or the storage 230. In some embodiments, each coil and/or supporter may be marked divisionally to be convenient for recognizing and application. For example, the parameters of the coil 510 and the supporter 520 may be determined and stored in the storage module 320, and when a user needs to use the coil 510 and the supporter 520 to scan a target body, the user may select the stored parameters of the coil 510 and the supporter 520, and the processor 210 may receive the selected parameters for further processing as described elsewhere in this disclosure.

In 1220, an attenuation correction (AC) map of the coil module 430 may be generated by the computing device 120 according to the parameter of the coil module 430. In some embodiments, the acquired attenuation coefficients of different absorbing materials may be assigned to a design map as pixel values, so that the AC map of the coil module 430 may be generated. The design map may be a map including the structure information of the coil module 430.

Figure 12:
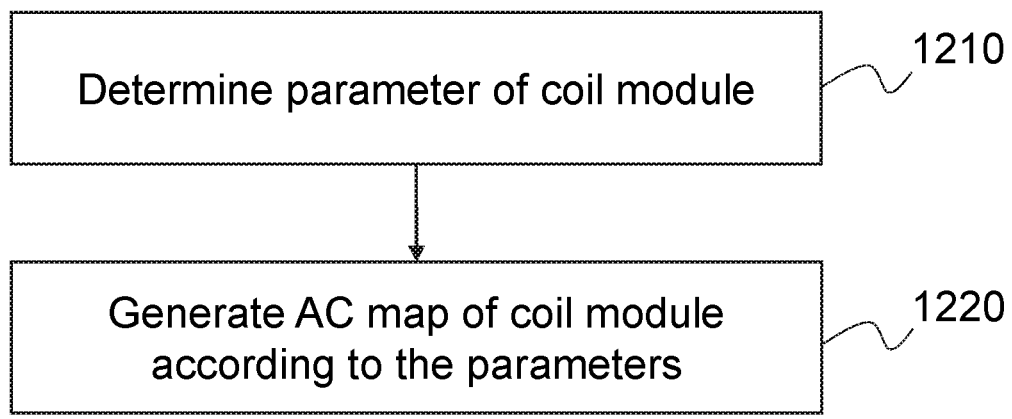
FIG. 12 is a flow chart of an exemplary AC generation process according to some embodiments of the present disclosure.

It should be noted that the simulation method illustrated in FIG. 12 may be used to generate an AC map of the bed 420 or other fixed components of the imaging device 110. Merely by way of example, if the material of the bed 420 or structure of the bed 420 are determined, attenuation coefficients of the material of the bed 420 may be acquired. Then the acquired attenuation coefficients may be assigned to a design map of the bed 420 as pixel values, so that the AC map of the bed 420 may be generated according to the assigned pixel values.

Return to FIG. 11, in 1120, the processor 220 may generate an AC map of a target body. The methods for AC map generation of the target body may be a transmission scanning. The transmission scanning method may include generating an AC map through a CT image, an MR image, and/or a PET image. Merely by way of example, the imaging device 110 may scan a target body by, for example, the scanner 410 and obtain an MR image or PET image. In some embodiments, the scanner 410 may be a single modality scanner or a multi-modality scanner that used in the imaging system 100 as illustrated in FIG. 1. For better understanding the present disclosure, a PET-MRI scanner may be described as an example of the scanner 410. When the target body is being scanned, the coil control module 330 may control the structure and movement of the coil module 430 depending on scanning parts of the target body. In some embodiments, the MRI and PET imaging process may be executed in one scanning cavity.

When scanning accomplished, the MR and/or PET image data captured may be processed and generate an AC map of the target body may be generated. In some embodiments, the processor 220 may process the captured MR and/or PET image data and generate the AC map of the target body. The MR image, the PET image, and/or the AC map may also be stored in a storage or may be sent to the computing device 120 through the network 130. In some embodiments, the AC map of the target body may be updated by the processor 220 according to feedback from a corrected image (e.g., a PET image). For example, if quality of a PET image after attenuation correction does not meet a requirement, the imaging module 340 may generate feedback to the attenuation correction module 350 to update AC map of the target body. The requirement may request analogy between two images generated in absent reconstruction below a threshold.

In 1130, the processor 220 may generate a final AC map. In some embodiments, the processor 220 may generate a final AC map based on the AC map of the coil module 430, the AC map of the bed 420 and the AC map of the target body. For example, the processor 220 may insert the AC map of the coil module 430 and the AC map of the bed 420 into the AC map of the target body to generate the final AC map. In an exemplary inserting process, the processor 220 may obtain a basis assisting to insert the AC map of the coil module 430 and the AC map of the bed 420 into the appropriate place of the AC map of the target body. In some embodiments, the basis may be a positon. For example, the processor 220 may obtain the positions of the coil module 430, the bed 420, and the target body according to the marker 530 or other measuring devices (e.g., a ruler, an infrared distance instrument, etc.). According to the obtained positions of the coil module 430, the bed 420, and the target body, the AC map of the coil module 430 and the AC map of the bed 420 may be inserted into the appropriate place of the AC map of the target body to generate a final AC map. The final AC map may be used to correct an image, for example, a PET image.

In 1140, the processor 220 may correct an image according to the final AC map. The correction procedure may be implemented in a computer software. The computer software may be MATLAB, C/C++, C#, VB, OPENCV, or some other kinds of imaging processing software. Take PET image attenuation correction as an example, the final AC map may be used to correct PET data firstly and the reconstruction may be performed to generate a PET image according to the corrected PET data. In some embodiments, the final AC map may be used in the process of PET image reconstruction. In some embodiments, the final AC map may be used to correct a PET image after reconstruction.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device" or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for conducting attenuation correction (AC) for an imaging device comprising a bed and a coil module, wherein the coil module comprises a flexible coil and an adjustable supporter configured to hold the flexible coil, and the coil module and the bed form a receiving space for receiving a target body, the method comprising:
   determining a configuration of the flexible coil based on a configuration of the adjustable supporter;
   obtaining, based on the configuration of the flexible coil and the configuration of the adjustable supporter, an AC map of the coil module;
   obtaining an AC map of the bed;
   obtaining an AC map of the target body;
   generating, based on the AC map of the coil module, the AC map of the bed, and the AC map of the target body, a final AC map; and
   correcting an image according to the final AC map.

2. The method of claim 1, wherein generating the final AC map comprises:
   obtaining a position of the coil module, a position of the bed, and a position of the target body; and
   inserting the AC map of the coil module and the AC map of the bed into the AC map of the target body according to the positions of the coil module, the bed, and the target body.

3. The method of claim 1, wherein obtaining the AC map of the coil module, obtaining the AC map of the bed, or obtaining the AC map of the target body is based on a PET image, an MR image, a CT image, or simulation.

4. The method of claim 1, wherein:
   at least one of obtaining the AC map of the coil module, obtaining the AC map of the bed, or obtaining the AC map of the target body is based on simulation, the simulation comprising:
   determining a parameter of a fixed component of the imaging device; and
   generating an AC map of the fixed component according to the parameter.

5. The method of claim 4, wherein the fixed component comprises the coil module or the bed.

6. The method of claim 4, wherein the parameter of the fixed component comprises at least one of a structure, a shape, or a material of the fixed component.

7. The method of claim 1, wherein
   at least a portion of obtaining the AC map of the coil module or obtaining the AC map of the bed is based on transmission scanning.

8. The method of claim 1, wherein
   the configuration of the flexible coil includes at least one of a structure, a shape, or a material of the flexible coil,
   the configuration of the adjustable supporter includes at least one of a structure, a shape, or a material of the adjustable supporter, and
   obtaining the AC map of the coil module is based on simulation, the simulation comprising;
   obtaining attenuation coefficients of the flexible coil and the adjustable supporter; and
   generating the AC map of the coil module according to the obtained attenuation coefficients and the configuration of the flexible coil and the configuration of the adjustable supporter.

9. The method of claim 1, wherein the flexible coil comprises a first fixture.

10. The method of claim 9, wherein the adjustable supporter comprises a second fixture configured to be connected with the first fixture.

11. The method of claim 10, wherein the flexible coil and the adjustable supporter connect to each other through an assembly of the first fixture and the second fixture.

12. The method of claim 11, wherein the assembly of the first fixture and the second fixture comprises at least one of buttoning, tying, sticking, or clasping.

13. The method of claim 1, wherein the adjustable supporter is configured to provide different rigid configurations by adjusting a structure or shape of the adjustable supporter.

14. The method of claim 1, further comprising updating the AC map of the target body based on the corrected image.

15. The method of claim 2, wherein the coil module further comprises a marker, and the method further comprising:
   determining, based on the marker, the position of the coil module, the position of the bed, and the position of the target body; and
   inserting the AC map of the coil module and the AC map of the bed into the AC map of the target body according to the obtained positions of the coil module, the bed, and the target body.

16. A system for conducting attenuation correction (AC) for an imaging device comprising a bed and a coil module, wherein the coil module comprises a flexible coil and an adjustable supporter configured to hold the flexible coil, and the coil module and the bed form a receiving space for receiving a target body, the system comprising:
   a storage device storing instructions, and
   a processor, when executing the instructions, configured to cause the system to perform operations including:
   determining a configuration of the flexible coil based on a configuration of the adjustable supporter;
   obtaining, based on the configuration of the flexible coil and the configuration of the adjustable supporter, an AC map of the coil module;

obtaining an AC map of the bed;
obtaining an AC map of the target body;
generating, based on the AC map of the coil module, the AC map of the bed, and the AC map of the target body, a final AC map; and
correcting an image according to the final AC map.

17. The system of claim 16, wherein obtaining the AC map of the coil module, obtaining the AC map of the bed, or obtaining the AC map of the target body is based on a PET image, an MR image, a CT image, or simulation.

18. The system of claim 16, wherein:
at least one of obtaining the AC map of the coil module, obtaining the AC map of the bed, or obtaining the AC map of the target body is based on simulation, the simulation comprising:
determining a parameter of a fixed component of the imaging device, wherein the parameter of the fixed component comprises at least one of a structure, a shape, or a material of the fixed component; and
generating an AC map of the fixed component according to the parameter.

19. The system of claim 16, wherein at least a portion of obtaining the AC map of the coil module or obtaining the AC map of the bed is based on transmission scanning.

20. The system of claim 16, wherein
the configuration of the flexible coil includes at least one of a structure, a shape, or a material of the flexible coil,
the configuration of the adjustable supporter includes at least one of a structure, a shape, or a material of the adjustable supporter, and
obtaining the AC map of the coil module is based on simulation, the simulation comprising;
obtaining attenuation coefficients of the flexible coil and the adjustable supporter; and
generating the AC map of the coil module according to the obtained attenuation coefficients and the configuration of the flexible coil and the configuration of the adjustable supporter.

21. The method of claim 9, wherein
the first fixture comprises a side coil box and a middle coil box,
the second fixture comprises a side fixation box and a middle fixation box, and
the coil boxes are configured to fit into the fixation boxes.

* * * * *